United States Patent [19]

Beddow

[11] 4,226,328

[45] Oct. 7, 1980

[54] CATHETERIZATION PACKAGE

[75] Inventor: David V. Beddow, Lake Villa, Ill.

[73] Assignee: Baxter Travenol Laboratories, Inc., Deerfield, Ill.

[21] Appl. No.: 28,516

[22] Filed: Apr. 9, 1979

[51] Int. Cl.³ .............................................. B65D 81/24
[52] U.S. Cl. .................................. 206/364; 206/571; 206/514; 206/560; 220/354; 220/408
[58] Field of Search ............... 206/363, 364, 365, 366, 206/546, 570, 571, 514, 560; 220/410, 408, 354, 6

[56] References Cited

U.S. PATENT DOCUMENTS

| | | | |
|---|---|---|---|
| 797,314 | 8/1905 | Owens | 220/408 X |
| 1,279,760 | 9/1918 | Richards, Jr. | 206/366 |
| 3,485,352 | 12/1969 | Pilger | 206/365 |
| 3,511,288 | 5/1970 | Sweet et al. | 220/355 X |
| 4,014,450 | 3/1977 | Girotti et al. | 220/355 |
| 4,091,953 | 5/1978 | Daenen | 220/355 X |
| 4,124,141 | 11/1978 | Armentrout et al. | 220/354 X |

FOREIGN PATENT DOCUMENTS 2037597  2/1972  Fed. Rep. of Germany .......... 206/216

Primary Examiner—Joseph Man-Fu Moy
Attorney, Agent, or Firm—Henry W. Collins; Eugene M. Cummings; Paul C. Flattery

[57] ABSTRACT

A single-use disposable catheterization package containing the components required for accomplishing a catheterization procedure includes an outer tray and an inner tray. During storage the inner tray is nested within the outer tray and the components required for the catheterization procedure are organized within respective recesses provided on the inner tray. Upon use, the trays are separated and liquid collected as a result of the procedure is received in the outer tray. To prevent spillage, the inner tray is inverted and attached to the outer tray to provide a closed compartment. Rim portions on the inner and outer trays provide a locking leak-resistant engagement between the trays.

2 Claims, 6 Drawing Figures

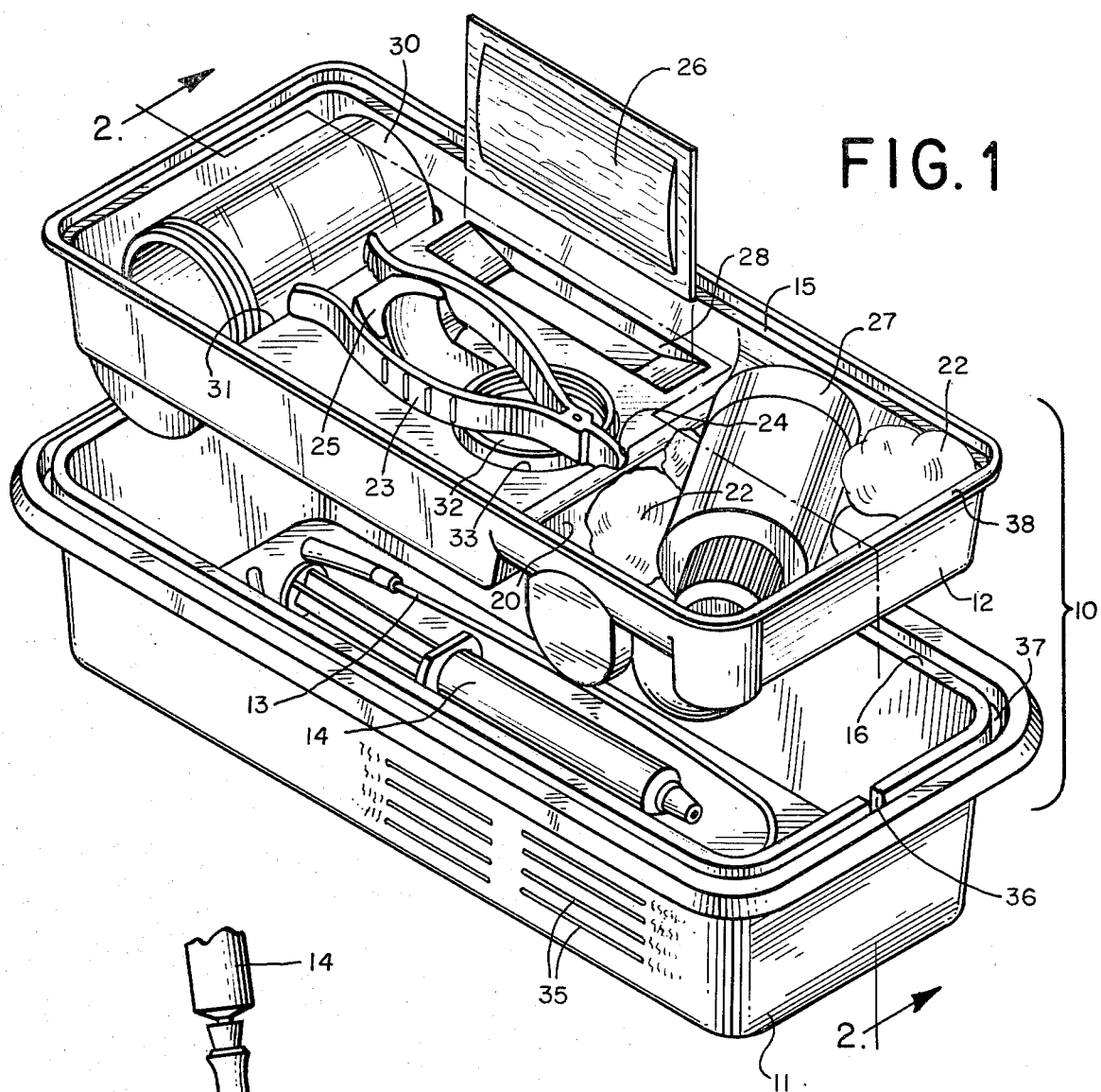
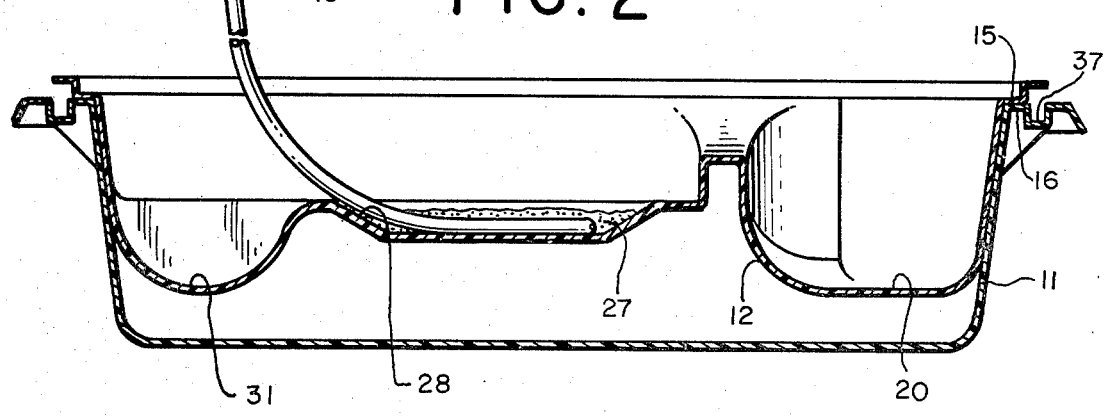
FIG. 1
FIG. 2

U.S. Patent  Oct. 7, 1980  Sheet 2 of 2  4,226,328
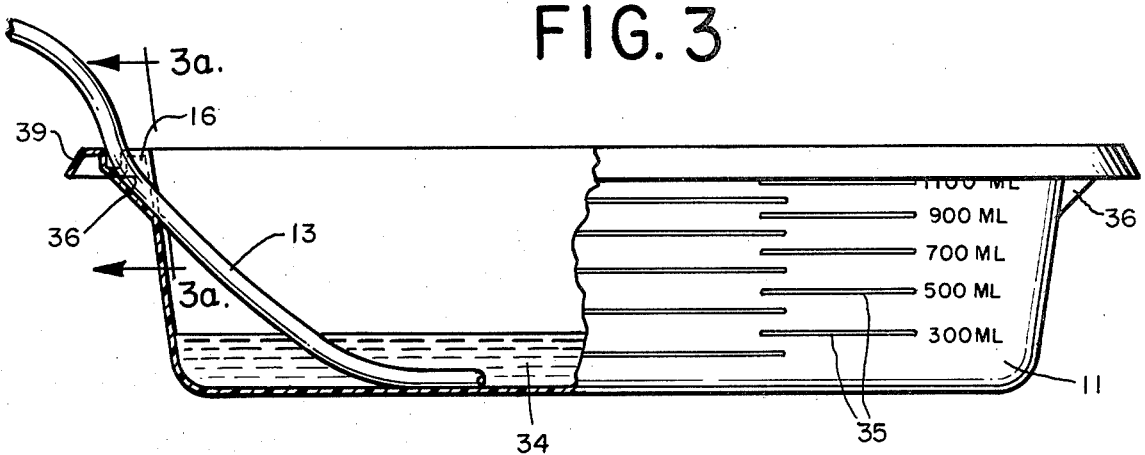
FIG. 3
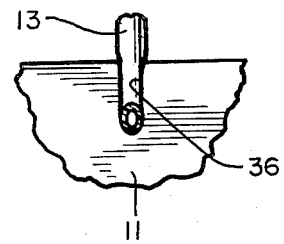
FIG. 3a
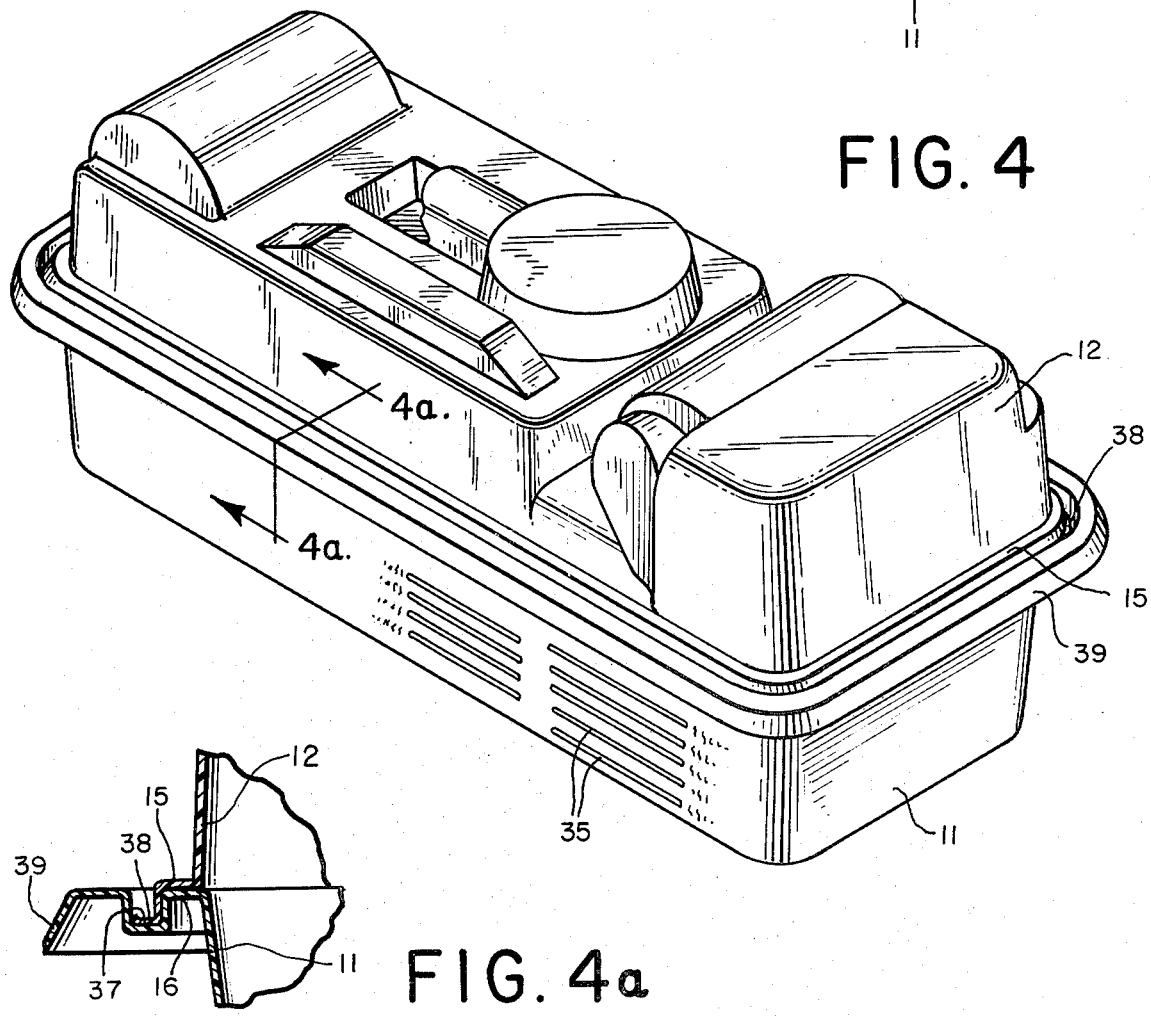
FIG. 4
FIG. 4a

CATHETERIZATION PACKAGE

BACKGROUND OF THE INVENTION

This invention relates generally to a catheterization package, and more particularly to a catheterization package which provides a closed container for liquids collected as a result of a catheterization procedure.

Single-use disposable catheterization packages generally consist of a tray in which all of the components necessary for accomplishing a catheterization procedure, including preparation items, catheter and collection bottle, are arranged in their preferred order of use. The tray is sealed in a suitable pouch so that in using the package the physician or nurse is assured that all items necessary for the procedure are present and in a sterile condition. Examples of prior art catheterization packages of this nature are described in U.S. Pat. Nos. 3,978,983, 3,851,649, 3,329,261, 3,166,189, 3,013,656 and 2,346,636.

Ordinarily, in a catheterization procedure it is desired to collect in a closed container a small sample of liquid for analysis, and prior art catheterization packages have typically included a small specimen bottle and cover for this purpose. However, no closed container has been provided in these packages for liquid collected in excess of that required for the sample, and the physician has heretofore been forced to either collect and transport the excess liquid in an open portion of the package housing, or to provide a separate closed container for this purpose.

The present invention is directed to a package construction which obviates this problem by providing a closed leak-resistant collection reservoir for the excess liquid. This is accomplished without adding additional components to the package, and at a reduction in cost compared to the expense of a separate container for this purpose.

Accordingly, it is a general object of the present invention to provide a new and improved catheterization package.

It is a more specific object of the present invention to provide an improved catheterization package which provides for collection of excess liquids in a closed spillresistant container.

SUMMARY OF THE INVENTION

The invention is directed to a catheterization package which includes an outer tray including a circumferential rim portion and an inner tray including a circumferential rim portion dimensioned to engage the rim portion of the outer tray whereby the inner tray is suspended within the outer tray during storage of the package, and a plurality of recesses on the top surface thereof for receiving the components of the catheterization package. To provide a closed leak-resistant container for liquid collected during use of the catheterization package, the rim portion of the inner tray is adapted for locking engagement with the rim portion of the outer tray when the inner tray is inverted and assembled over the outer tray.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a catheterization package constructed in accordance with the invention showing the inner and outer tray portions thereof separated prior to use.

FIG. 2 is a cross-sectional view taken along line 2—2 of FIG. 1 showing the catheter of the catheterization package being lubricated prior to use.

FIG. 3 is a side elevational view of the outer tray portion of the catheterization package partly in cross-section to show the collection of liquid therein.

FIG. 3a is an enlarged perspective view of a portion of the bottom tray showing the attachment between the catheter tubing and the outer tray during collection of liquid.

FIG. 4 is a perspective view of the catheterization package showing the inner and outer tray portions thereof assembled following the catheterization procedure to provide a closed reservoir for collected liquid.

FIG. 4a is an enlarged cross-sectional view of the interlocking rims of the inner and outer trays when assembled as shown in FIG. 4.

DESCRIPTION OF THE PREFERRED EMBODIMENT

Referring to the Figures, and particularly to FIG. 1, a catheterization package 10 constructed in accordance with the invention is seen to include a generally rectangular box-like outer tray 11 having an open top within which a generally rectangular inner tray 12 is suspended. Prior to use, the assembled inner and outer trays are preferably enclosed within an appropriately dimensioned pouch (not shown), which is sealed to maintain the sterility of the components within the catheterization package. The pouch may be formed of a transparent and flexible plastic film and an appropriate wrapping may be provided between the assembled trays and the pouch. The various foldable materials required for the catheterization procedure, including a water proof underpad (not shown), a pair of pre-powdered gloves (not shown), and protective drape (not shown) may be arranged in a flat condition between the wrap and the trays.

Prior to use, the plastic pouch is opened and the wrap, underpad, plastic gloves and drape are removed, unfolded and placed in position on the patient in a manner well known to the art. Inner tray 12 is then lifted from outer tray 11, as shown in FIG. 1, exposing the catheter 13 and syringe 14 for use. As best shown in FIG. 2, the inner tray 12 includes a flat horizontal rim portion 15 which engages a similarly dimensioned horizontal rim portion 16 on outer tray 11. The base and tray portions may be thermoformed by conventional methods from a thin plastic material.

Inner tray 12 is formed with a plurality of compartments or recesses which accommodate the various components required by the catheterization procedure. A first recess 20 is provided to accommodate a bottle 21 of cleansing solution, and to hold the bottle in place the recess may include an appropriately dimensioned section at one end for receiving the neck and cap of the bottle, and an appropriately dimensioned section at its other end to receive the bottom end of the bottle. Recess 20 may include a central section which is wider than bottle 21 to facilitate access to the bottle, and to provide an area for storing balls of cleansing material 22, which are used in preparing the patient for catheterization. Prior to use the balls of cleansing material are saturated with cleansing solution by removing bottle 21 from compartment 20, and pouring the contents of the bottle over the balls of cleansing material while the balls are in their stored position in recess 20. After saturization, the balls are handled by a forceps 23 which is securely stored in tray 12 by means of a notch 24 and abutment 25 provided on the tray surface.

To provide for lubrication of the catheter, the catheterization package 10 includes an individually sealed foil container 26 of lubricating jelly 27 packed within an elongated rectangular recess 28. In use, this container is removed from recess 27 and torn open, and the lubricating jelly contained therein is deposited in the recess. Catheter 13 and syringe 14 are now removed from outer tray 11 and prepared for use. After the patient has been prepared, the catheter is lubricated with the lubricating jelly 27 by positioning the catheter tip in the jelly-filled recess 28, as shown in FIG. 2, and the catheterization procedure is carried out in a conventional manner.

A sample of liquid collected as a result of the catheterization procedure may be collected in a specimen bottle 30 (FIG. 1) which is contained in a recess 31 in the inner tray. A cap 32, which is in a recess 33 in the inner tray, is utilized to close the specimen bottle.

As shown in FIG. 3, after the desired specimen has been collected in specimen bottle 30, the excess collected liquid 34 is collected in outer tray 11. A plurality of volume-indicating marks 35 may be provided in embossed or printed form on one or more side walls of the outer tray to indicate the volume of liquid collected. Although marks reading from 300 milliliters to 1100 milliliters are shown in the preferred embodiment, it will be appreciated that other volumetric indications may be provided to accommodate various sizes of outer trays and units of volume.

The rim of outer tray 11 may be provided with one or more channels 36 to secure the end of catheter 13 during collection of fluid in the tray. As seen in FIG. 3, these channels extend between the rim and sidewall portions of tray 11, and, as such provide an angled walled bridge element which firmly grips the catheter tubing and adds to the rigidity of the tray. As best seen in FIG. 3a, the walls of the channel are preferably spaced to slightly compress the catheter tubing so as to prevent the tubing from being inadvertently pulled loose during collection of liquid 34.

After the excess liquid has been collected in outer tray 11, the outer tray may be conveniently closed by inverting inner tray 12 and securing the two trays together as shown in FIG. 4. The result is an enclosed container for the collected liquid 34 which may be transported for storage or disposal without risk of the liquid being spilled. As illustrated in FIG. 4a, a leak-resistant interlocking fit is obtained between the two trays by providing a circumferential channel 37 on the rim portion of tray 11 within which a circumferential lip portion 38 provided on the rim portion of tray 12 is received. In practice, the channel and lip portions are dimensioned to obtain an engagement which is sufficiently tight to resist leakage and prevent inadvertent separation, but not so tight as to present difficulty to the physician or nurse in assembling or disassembling the trays.

To provide a smooth edge for handling purposes, a rounded circumferential flange portion 39 is provided on tray 11 external to channel 37. This flange portion is angled downwardly with respect to the top surface of the tray, and as shown in FIG. 4a, is cut at an angle in a vertical plane such that an edge free of potentially abrasive corners is obtained. The resulting rim construction adds additional rigidity to tray 11 and provides convenient handle means for carrying the tray.

Thus, a sterile one-use catheterization package has been described which includes all of the components necessary to carry out a catheterization procedure. An inner tray portion of this package stores the components so as to provide protection against damage during shipment and to render the components readily available when called for by the procedure. An outer tray portion provides a similar storage function for the catheter and syringe, and doubles as a closed spill-resistant container for liquid collected as a result of the procedure. The inner and outer trays may be conveniently and economically formed by conventional thermoforming techniques of thin molded plastic, the various recesses provided therein serving to enhance the overall structural strength of the trays.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A disposable catheterization package of the type containing components for a catheterization procedure, comprising:

an outer tray including side walls and a circumferential rim portion;

an inner tray including a circumferential rim portion dimensioned to engage said outer tray rim portion whereby said inner tray is nestingly suspended within said outer tray during storage of said package, said inner tray including a plurality of recesses on the surface thereof for receiving at least a portion of the components contained in the package;

said outer tray rim portion including a channel and inner and outer generally flat horizontal flange portions on either side of said channel;

said inner tray rim portion including a flat horizontal flange portion and a lip portion upstanding therefrom;

said inner flange portion of said outer tray rim and said flange portion of said inner tray rim being disposed for engaging in an abutting relationship when said inner tray is nested within said outer tray;

a notch-like recess along said inner flange portion of said outer tray rim for receiving in supporting relationship a portion of a catheter used in the catheterization procedure;

said lip portion of said inner tray rim being receivable within said channel of said outer tray rim when said inner tray is inverted, to provide a closed spill-resistant container between said tray portions for liquid collected during the catheterization procedure.

2. A disposable catheterization package in accordance with claim 1 wherein the edge of said outer flange portion of said outer tray rim is downturned.

* * * * *